(12) United States Patent
Smith

(10) Patent No.: US 9,370,373 B2
(45) Date of Patent: Jun. 21, 2016

(54) SURGICAL TOOL FOR LSS DECOMPRESSION

(71) Applicant: KYPHON SARL, Neuchatel (CH)

(72) Inventor: Michael A. Smith, San Jose, CA (US)

(73) Assignee: KYPHON SÀRL, Neuchâtel (CH)

( * ) Notice: Subject to any disclaimer, the term of this patent is extended or adjusted under 35 U.S.C. 154(b) by 3 days.

(21) Appl. No.: 14/695,224

(22) Filed: Apr. 24, 2015

(65) Prior Publication Data

US 2015/0223823 A1    Aug. 13, 2015

Related U.S. Application Data

(63) Continuation of application No. 13/793,302, filed on Mar. 11, 2013, now Pat. No. 9,050,109.

(51) Int. Cl.
| | |
|---|---|
| *A61B 17/16* | (2006.01) |
| *A61B 18/18* | (2006.01) |
| *A61B 18/14* | (2006.01) |
| *A61B 18/04* | (2006.01) |
| *A61B 17/32* | (2006.01) |
| *A61B 18/00* | (2006.01) |
| *A61B 17/00* | (2006.01) |

(52) U.S. Cl.
CPC ......... *A61B 17/1611* (2013.01); *A61B 17/1604* (2013.01); *A61B 17/32* (2013.01); *A61B 18/1442* (2013.01); *A61B 18/1447* (2013.01); *A61B 18/042* (2013.01); *A61B 2017/00473* (2013.01); *A61B 2017/320044* (2013.01); *A61B 2017/320064* (2013.01); *A61B 2018/00565* (2013.01); *A61B 2018/00601* (2013.01); *A61B 2018/146* (2013.01); *A61B 2217/005* (2013.01)

(58) Field of Classification Search
None
See application file for complete search history.

(56) References Cited

U.S. PATENT DOCUMENTS

| | | | |
|---|---|---|---|
| 4,832,683 | A | 5/1989 | Idemoto et al. |
| 5,085,657 | A | 2/1992 | Ben-Simhon |
| 5,385,570 | A | 1/1995 | Chin et al. |
| 5,653,713 | A | 8/1997 | Michelson |
| 5,766,177 | A | 6/1998 | Lucas-Dean et al. |
| 5,925,050 | A | 7/1999 | Howard, III |
| 6,348,051 | B1 | 2/2002 | Farin et al. |
| 6,379,350 | B1 | 4/2002 | Sharkey et al. |
| 6,520,979 | B1 | 2/2003 | Loubens et al. |
| 6,685,710 | B2 | 2/2004 | Agbodoe et al. |
| 6,802,842 | B2 | 10/2004 | Ellman et al. |
| 7,303,559 | B2 | 12/2007 | Peng et al. |
| 7,615,053 | B2 | 11/2009 | McKinley |
| 8,177,783 | B2 | 5/2012 | Davison et al. |
| 8,657,823 | B2 | 2/2014 | Agbodoe |
| 8,690,038 | B2 | 4/2014 | Daumuller |
| 8,808,319 | B2 | 8/2014 | Houser et al. |
| 2003/0181904 | A1 | 9/2003 | Levine et al. |
| 2004/0097919 | A1 | 5/2004 | Wellman et al. |
| 2004/0162553 | A1 | 8/2004 | Peng et al. |
| 2010/0023007 | A1 | 1/2010 | Sartor et al. |
| 2010/0036370 | A1 | 2/2010 | Mirel et al. |
| 2014/0188139 | A1 | 7/2014 | Fallin et al. |

*Primary Examiner* — Brian T Gedeon
(74) *Attorney, Agent, or Firm* — Martin & Ferraro LLP

(57) ABSTRACT

A cutting device includes a lower jaw extending between a proximal end and a distal end. The distal end terminates with a cavity and a blunt tip. An upper jaw extends between and proximal end a distal end. The upper jaw is configured for translation along the lower jaw. The upper jaw includes a cutting tip configured to cut bone.

12 Claims, 3 Drawing Sheets

SURGICAL TOOL FOR LSS DECOMPRESSION

The present application is a continuation of application Ser. No. 13/793,302, filed Mar. 11, 2013; all of which is incorporated herein by reference.

The present invention relates generally to devices and methods for cutting a material or substance. More specifically, the devices and methods are useful for resecting nerve and/or soft tissue via a minimally invasive procedure to alleviate pain.

BACKGROUND

Standard methods of cutting tissue may include using a scalpel, scissors, and radio frequency energy. Electrosurgical procedures and techniques using radio frequency energy are currently used since they generally reduce patient bleeding and trauma associated with cutting operations. Additionally, electrosurgical ablation procedures, where tissue surfaces and volume may be reshaped, cannot be duplicated through other treatment modalities.

Minimally invasive procedures in nerve and/or soft tissue such as the spine or the breast, however, are difficult to perform using standard scissors and scalpel. Furthermore, in a closed environment, radio frequency current dissipates into the surrounding tissue causing a decreased ability to achieve a current at the cutting electrode of sufficiently high density to initiate a cut. To overcome this problem, high power settings are often required to initiate the cut which often is painful and increases thermal damage to the tissue whether using a standard or a custom electrosurgical generator.

Another problem associated with cutting tissue is the control of bleeding. Radio frequency energy controls bleeding by coagulating small blood vessels. Another method of controlling bleeding is through the use of heat. For example, some commercially available scalpels use direct heat to control bleeding. However, while the bleeding is generally controlled, the cutting of tissue is often slower than with radio frequency energy and the knife edge readily dulls. Other commercially available scalpels use ultrasonic energy generally at 50 kHz to heat the tissue so as to coagulate severed blood vessels but cut slower than a standard electrosurgical electrode and are costly as a custom ultrasonic generator is required.

A further disadvantage of using radio frequency energy is the generation of smoke. The smoke is malodorous and can contain airborne viral particles that may be infectious. Furthermore, the smoke often obscures visualization of the procedure. When the smoke becomes too dense, the procedure is delayed until the smoke is released through one of the trocar ports and after enough carbon dioxide gas has reinsufflated the abdominal cavity. This unnecessarily prolongs the operative time.

Radiofrequency (RF) energy is used in a wide range of surgical procedures because it provides efficient tissue resection and coagulation and relatively easy access to the target tissues through a portal or cannula. Conventional monopolar high frequency electrosurgical devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Present electrosurgical techniques used for tissue ablation may suffer from an inability to provide the ability for fine dissection of soft tissue. The distal ends of electrosurgical devices are wide and flat, creating a relatively wide area of volumetric tissue removal and making fine dissections along tissue planes difficult to achieve because of the lack of precision provided by the current tip geometries.

In addition, identification of the plane is more difficult because the large ablated area and overall size of the device tip obscures the physician's view of the surgical field. The inability to provide for fine dissection of soft tissue is a significant disadvantage in using electrosurgical techniques for tissue ablation, particularly in arthroscopic, otolaryngological, and spinal procedures.

Traditional monopolar RF systems can provide fine dissection capabilities of soft tissue, but may also cause a high level of collateral thermal damage. Further, these devices may suffer from an inability to control the depth of necrosis in the tissue being treated. The high heat intensity generated by these systems causes burning and charring of the surrounding tissue, leading to increased pain and slower recovery of the remaining tissue. Further, the desire for an electrosurgical device to provide for fine dissection of soft tissue may compromise the ability to provide consistent ablative cutting without significant collateral damage while allowing for concomitant hemostasis and good coagulation of the remaining tissue.

Another problem with currently available RF nerve ablation devices is that they attempt to destroy nerve tissue from a central location including the tip of the device and a 3-D spherical or cylindrical zone around it. As a result, the further away the resecting ability is from the central zone the less effective the nerve destruction. Consequently, often the nerve is not adequately ablated leading to continued pain symptoms.

Further, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue.

Other devices such as mechanical rongures can be used to remove soft tissue. However, these devices require the insertion of relatively large cannulas that further complicate the surgical procedure and can cause nerve compression and pain with variable clinical efficacy.

Accordingly, there is a need for devices and methods to provide efficient severing or cutting of nerve and/or soft tissue that can be used during a minimally invasive procedure and/or during an open surgical procedure. Further, there is also a need for devices and methods that provide fine dissection capabilities of nerve and/or soft tissue. Devices and methods that do not cause a high level of collateral thermal damage and allow for the control of necrosis in the tissue being treated are also needed. Devices and methods that provide efficient, controlled and safe debulking of tissue would also be beneficial.

SUMMARY

This application is directed to a cutting device, in accordance with the principles of this disclosure, which includes a lower jaw extending between a proximal end and a distal end. The distal end terminates with a cavity and a blunt tip. An upper jaw extends between and proximal end a distal end. The upper jaw is configured for translation along the lower jaw. The upper jaw includes a cutting tip configured to cut bone.

In one embodiment, a cutting device as recited includes a probe extending between a proximal end and a distal end. The distal end terminates with a cavity and a blunt tip. A sleeve extends between a proximal end and a distal end and is configured for translation along the probe. The probe includes a radio frequency cutting tip configured to cut bone.

In one embodiment, a method of cutting tissue includes providing a cutting device including a probe extending between a proximal end and a distal end, the distal end terminating with a cavity and a blunt tip. A sleeve is extended between a proximal end and a distal end and configured for translation along the probe. The probe includes a radio frequency cutting tip configured to cut bone. Soft tissue is pulled towards the cavity to cut the tissue with the cutting tip. Bone is cut with the cutting tip of the sleeve by translating the sleeve along the probe in a distal direction.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

DETAILED DESCRIPTION

Figure 1:
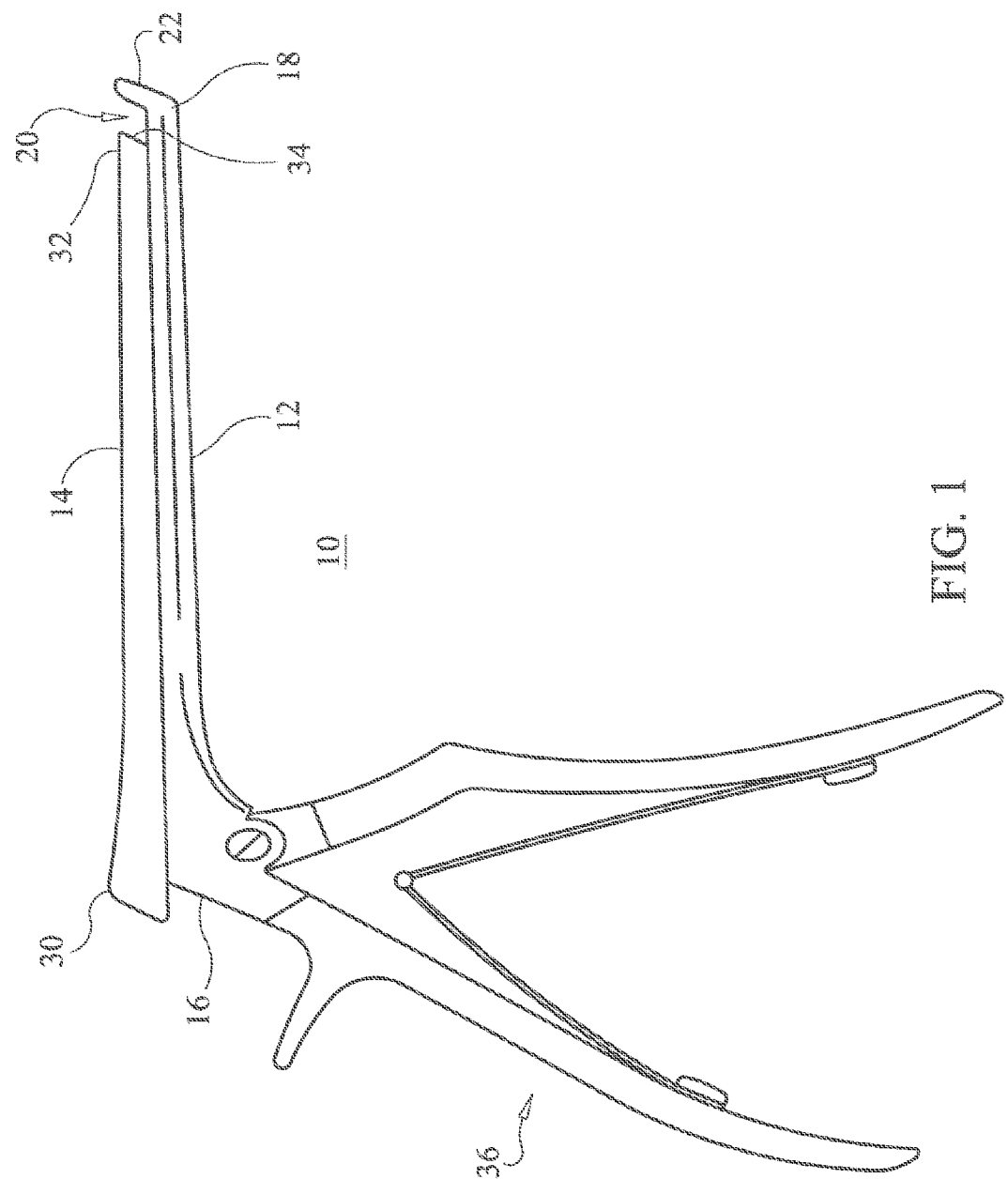
FIG. 1 is a side view of an embodiment of the device in accordance with the principles of the present disclosure.

Devices for efficient severing or cutting of a material or substance such as nerve and/or soft tissue suitable for use in open surgical and/or minimally invasive procedures are disclosed. The following description is presented to enable any person skilled in the art to make and use the present disclosure. Descriptions of specific embodiments and applications are provided only as examples and various modifications will be readily apparent to those skilled in the art.

In one embodiment, a cutting device combines bone cutting and soft tissue PEAK plasma removal with suction. In one embodiment, cutting is accomplished by the PEAK probe cutter as the cutter pulls tissue towards the RF portion, so as to simulate a Kerrison rongeur. The RF power will not cut bone, therefore, in one embodiment, an outer sleeve with distal cutting tip is provided to cut bone. The sleeve is configured to capture bony tissue and then be removed and cleaned like a standard Kerrison rongeur. The combination tool simplifies decompression for the surgeon by allowing them to perform all cutting with one tool minimizing changing of tools. In one embodiment, the device cutting tips are disposable therefore would always be sharp unlike Kerrisons which become dull. In one embodiment, the sleeve and probe can be removed from the handle for cleaning and/or use with other handles.

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof) means rearward or away from the direction of the forward, distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

For purposes of the description contained herein, "vacuum" means pressure within a space that is lower than atmospheric or ambient pressure by any amount, and although not exclusive of a condition of absolute vacuum defined by a complete absence within a space of air, fluid or other matter, the term as used herein is not meant to require or be limited to such a condition.

The headings below are not meant to limit the disclosure in any way; embodiments under any one heading may be used in conjunction with embodiments under any other heading.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Radiofrequency (RF) ablation devices have been available to surgeons to treat many medical conditions, for example, in the treatment of tumors in lung, liver, kidney, bone and other body organs. Pulsed RF has also been used for treatment of tumors, cardiac arrhythmias, chronic and post-operative pain, bone fracture and soft tissue wounds.

The components of the cutting device can be fabricated from biologically acceptable materials suitable for medical apparatuses, including metals, synthetic polymers, ceramics, thermoplastic and polymeric material and/or their composites. For example, the components of the holding device, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan, Fe—Mn—Si and Fe—Ni—Co—Ti composites), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaS04 polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, and composites of metals and calcium-based ceramics, composites of PEEK and calcium based ceramics, and combinations of the above materials.

Various components of the holding device may have material composites, including the above materials, to achieve various desired characteristics such as strength, rigidity, elasticity, compliance, and biomechanical performance, durability and to provide a non-stick surface. The components of the holding device may be monolithically formed, extruded, coextruded, hot molded, cold molded, press molded, integrally connected or include fastening elements and/or coupling components, as described herein.

Figure 2:
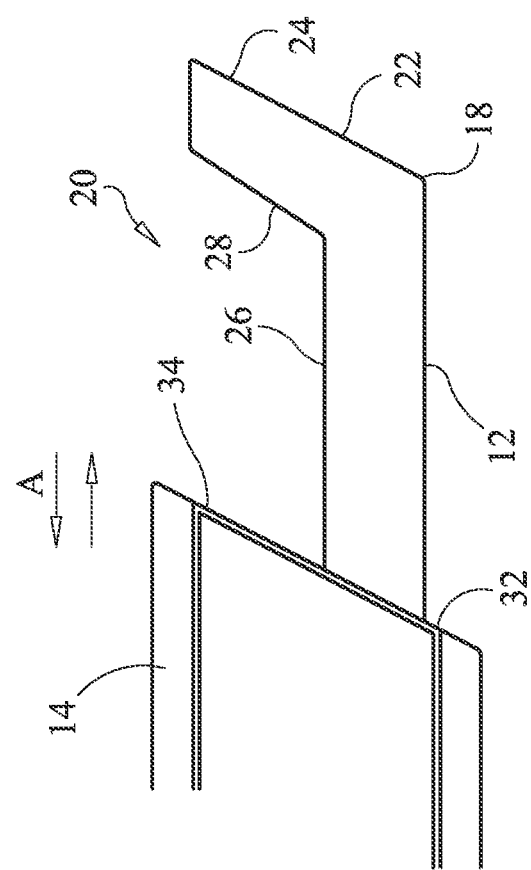
FIG. 2 is an enlarged view of components of the device shown in FIG. 1.
Figure 3:
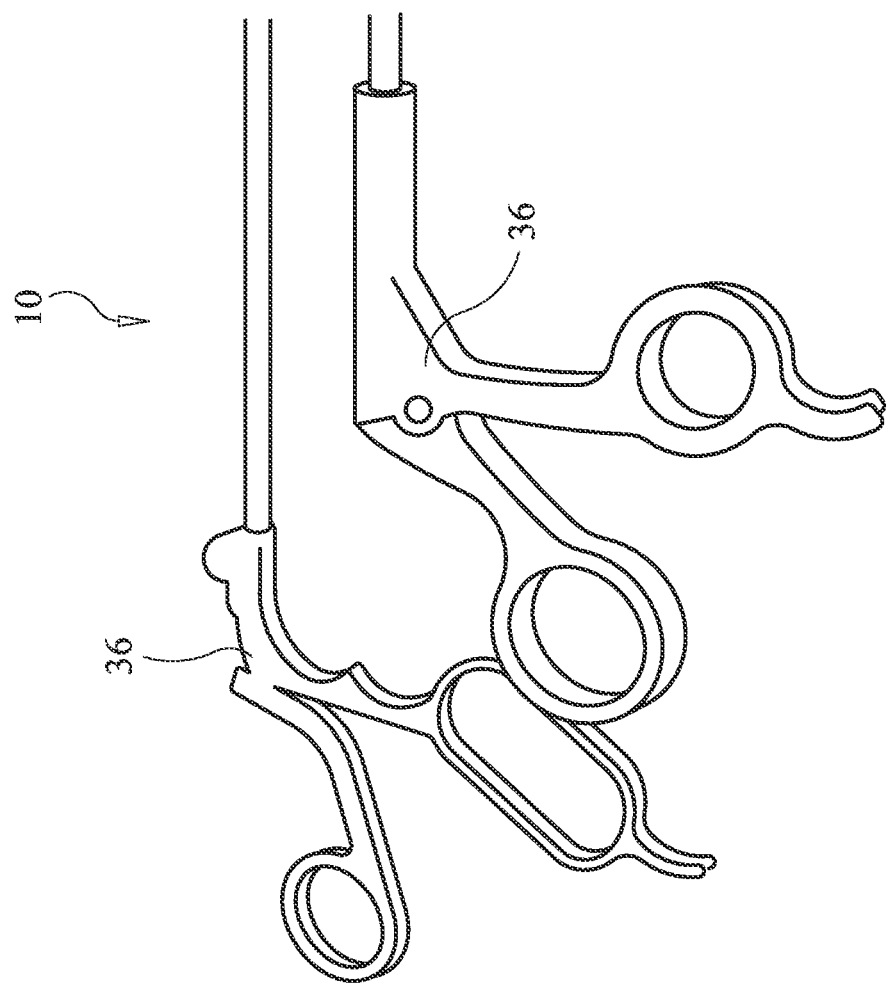
FIG. 3 shows variations of handles that can be used with the device of FIG. 1.

The following discussion includes a description of a surgical device for cutting and removal of soft tissue and/or bone tissue and related methods of employing the device in accordance with the principles of the present disclosure. Alternate embodiments are also disclosed. Reference will now be made in detail to the exemplary embodiments of the present disclosure, which are illustrated in the accompanying figures. Turning now to FIGS. 1-3, there are illustrated components of the surgical device for cutting and removal of soft tissue and/or bone tissue in accordance with the principles of the present disclosure.

In one embodiment, as shown in FIGS. 1-2, the cutting device 10 includes a lower jaw, such as, for example, a probe 12 and an upper jaw, such as, for example, a sleeve 14. Probe 12 extends between a proximal end 16 and a distal end 18. Probe 12 includes blunt tip 22 positioned at end 18. Sleeve 14 extends partially along probe 12 such that sleeve 14 terminates at cavity 20. In one embodiment, probe 12 is a hollow needle having blunt tip 22. Tip 22 includes an outer surface 24, which may be rounded and/or somewhat pointed to allow for easy penetration through tissue. In one embodiment, probe 12 is operatively connected to semi-steerable or navigational sources for easier guidance into tissues. In one embodiment, the navigational source is coupled with a pre-procedure imaging means such as for example, CT, MRI, PET scan, etc. so that the target nerve or soft tissue to be cut can be identified and accurately located during the procedure.

Cavity 20 is positioned at distal end 18, and 20 extends proximally from tip 20 along probe 12. Cavity 20 includes an inner surface 26 that defines an inner edge 28 of cavity 20. Edge 28 is configured to cut and capture tissue and/or bone. Cavity 20 is configured to receive tissue and/or bone as edge 28 separates tissue. Cavity 20 can have any shape allowing for nerve and/or soft tissue to be pulled back into cavity 20 and ablated or resected with pulsed plasma and/or radio frequency discharges. As shown in FIG. 2, cavity 20 is scoop shaped. In various embodiments, cavity 20 is shaped as a regular or irregular polygon including arcuate, c-shaped, round, square, oblong, kidney shaped, crescent, or beveled shape with or without ridges. In one embodiment, sleeve 14 and probe 12 form a hollowed out conduit such that cavity 20 receives and emits pulsed plasma or RF discharges adapted for cutting nerve and/or soft tissue. In one embodiment, probe 12 is coated in an electrically insulated layer adjacent to and exposing cavity 20 such that the energy transmitted from the RF frequency and/or the plasma is centralized in cavity 20. In some embodiments, the coating or insulating layer can be glass or ceramic having a thickness from about 0.005 to about 0.5 mm thick or from about 0.01 to about 0.2 mm thick. The insulation extends to the proximal end of probe 12 or partially along probe 12.

In one embodiment, probe 12 includes an internal passage configured to engage a vacuum (not shown) to remove nerve and/or soft tissue that is resected as RF current is applied. Alternatively, an additional channel is possible for delivering fluid to the surgical site. At its proximate end, probe 12 is operatively connected to the vacuum to provide suction to resected nerve and/or tissue. Any suitable aspirator, cylindrical or otherwise, or other mechanism that creates vacuum upon the movement of an actuating member thereof, may be utilized as a vacuum source, such as, for example, a syringe or a mechanical vacuum. In one embodiment, the vacuum is in communication with cavity 20 for providing suction to remove cut nerve and/or soft tissue.

Sleeve 14 extends between proximal end 30 and distal end 32. Sleeve 14 is configured for translation along probe 12. In one embodiment, sleeve 14 encases probe 12. In another embodiment, sleeve 14 is releasably engaged with a portion of probe 12. Distal end 32 includes a cutting tip 34 configured to cut bone. Sleeve 14 is configured such that it translates along a distal portion of probe 12 such that as cutting tip 34 moves towards distal edge 28, cutting tip 34 cuts bone. The bone is then captured in cavity 20.

In one embodiment, handle 36 is configured for disposal with proximal ends 16, 30 of probe 12 and sleeve 14, respectively. Handle 36 is configured to facilitate translation of sleeve 14 along probe 12. In one embodiment, a Kerrison type handle can be utilized. Those skilled in the art will recognize that any type of suitable handle may be utilized, such as, for example, a pistol grip handle or a scissors handle. In one embodiment, probe 12 and sleeve 14 are detachable from handle 36 such that probe 12 and sleeve 14 are disposable and/or or removeable for cleaning. In one embodiment, handle 36 is plastic such that the entire device could be disposable.

In operation, assembly and use, device 10 is employed with a surgical procedure for cutting and removal of soft tissue and/or bone tissue. The device 10 is inserted into or on the anatomy of a patient. The distal region of probe 12 of cutting device 10 is positioned adjacent a nerve or soft tissue to be cut. Tip 22 of distal end 18 is blunt so as not to pierce certain areas of the patient, such as, for example, the spinal cord. Cavity 20 is moved over the nerve and/or soft tissue to be cut. A medical practitioner cuts the tissue and the resected tissue is removed by suction. Cavity 20 is in communication with a vacuum to remove the cut nerve and/or soft tissue. In addition to cutting soft tissue, device 10 is configured to cut bone. To cut bone, sleeve 14 is translated distally along probe 12 as shown by arrow A. As sleeve 14 translates along probe 12, cutting tip 34 of sleeve 14 is sharp enough to cut bone, which is then captured in cavity 20. Cavity 20 is in communication with a vacuum to remove the resected tissue and/or bone from probe 12 such that additional tissue and/or bone can be cut and captured in cavity 20.

In another embodiment, cutting device 10 defines a small channel configured for injection of irrigation fluid to the surgical site to wash out the surgical site. The irrigation fluid may also facilitate suction of loose tissue fragments, and/or cool ablated tissue.

In one embodiment, probe 12 is operatively coupled to a source of navigational capability to facilitate guidance through the tissues. In various embodiments, the methods of cutting disclosed herein can include a pre-procedure step wherein the probe or needle can be coupled to a CT, MRI, PET machine, or the like so that the target nerve and/or soft tissue to be cut can be identified and accurately located during the resection procedure.

The methods for cutting described hereinabove allow complete resection of the nerve avoiding the problems and partial effectiveness of current RF and cryoablation devices available in the art, and also allow for easier, more efficient, more complete, and safer removal of soft tissue that is causing stenosis pain symptoms.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A cutting device comprising:
   a lower jaw extending between a proximal end and a distal end, the distal end terminating with a cavity and a tip;
   an upper jaw extending between a proximal end and a distal end and configured for translation along the lower jaw, the upper jaw includes a cutting tip configured to cut bone, the upper jaw being an outer sleeve and the lower jaw being configured for translation in and out of the sleeve.

2. A cutting device as recited in claim 1, further comprising a handle disposed at the proximal ends of the outer sleeve and lower jaw and the outer sleeve being engaged with the lower jaw such that the outer sleeve translates along the lower jaw to cut bone.

3. A cutting device as recited in claim 1, wherein the lower jaw is a probe.

4. A cutting device as recited in claim 1, wherein the cavity is configured to receive tissue.

5. A cutting device as recited in claim 1, wherein the cavity includes an inner surface defining a distal edge configured to cut and capture bone.

6. A cutting device as recited in claim 1, wherein the cavity is scoop shaped and is configured for resecting and/or debulking tissue.

7. A cutting device as recited in claim 1, wherein the distal end of the lower jaw includes a radio frequency tip configured to cut tissue.

8. A cutting device as recited in claim 1, wherein the lower jaw includes a plasma tip for destruction of tissue.

9. A cutting device as recited in claim 2, wherein the upper and lower jaws are detachable from the handle.

10. A cutting device as recited in claim 1 further including an attachment to a vacuum to produce suction to remove tissue from the cavity.

11. A cutting device as recited in claim 7, wherein the lower jaw includes an electrically insulated layer adjacent to and exposing the cavity such that the energy transmitted from the radio frequency tip is centralized in the cavity.

12. A cutting device as recited in claim 1, wherein the tip is a blunt tip.

\* \* \* \* \*